United States Patent
Adamski

(10) Patent No.: US 7,342,230 B2
(45) Date of Patent: Mar. 11, 2008

(54) TERAHERTZ IMAGING SYSTEM AND ASSOCIATED METHOD

(75) Inventor: John L. Adamski, Kenmore, WA (US)

(73) Assignee: The Boeing Company, Chicago, IL (US)

( * ) Notice: Subject to any disclaimer, the term of this patent is extended or adjusted under 35 U.S.C. 154(b) by 75 days.

(21) Appl. No.: 11/185,154

(22) Filed: Jul. 20, 2005

(65) Prior Publication Data

US 2007/0085009 A1    Apr. 19, 2007

(51) Int. Cl.
  G01J 5/02    (2006.01)
  H01S 3/00    (2006.01)
  H05H 9/00    (2006.01)
(52) U.S. Cl. .............. 250/341.8; 372/2; 315/505; 378/146
(58) Field of Classification Search .......... 372/2; 315/505, 5.18; 378/146; 250/341.8
See application file for complete search history.

(56) References Cited

U.S. PATENT DOCUMENTS

| | | | |
|---|---|---|---|
| 5,099,175 A * | 3/1992 | Schlueter et al. | 315/4 |
| 5,960,013 A * | 9/1999 | Sheffield | 372/2 |
| 6,753,662 B1 * | 6/2004 | Krafft | 315/505 |
| 6,844,688 B1 * | 1/2005 | Williams et al. | 315/505 |
| 2002/0191650 A1 * | 12/2002 | Madey et al. | 372/2 |
| 2003/0178584 A1 * | 9/2003 | Arnone et al. | 250/495.1 |
| 2003/0179784 A1 * | 9/2003 | Minehara et al. | 372/2 |
| 2006/0022140 A1 * | 2/2006 | Connelly et al. | 250/338.1 |
| 2006/0039417 A1 * | 2/2006 | Biedron et al. | 372/2 |
| 2006/0214107 A1 * | 9/2006 | Mueller | 250/341.8 |

OTHER PUBLICATIONS

*Handheld terahertz wand to unmask terrorists*; Jul. 12, 2004, Exclusive from New Scientist Print Edition, Duncan Graham-Rowe; 2 pages available at http://www.newscientist.com/article.ns?id=dn6118&print=true (visited Jun. 3, 2005).

* cited by examiner

*Primary Examiner*—David Porta
*Assistant Examiner*—Mark R Gaworecki
(74) *Attorney, Agent, or Firm*—Alston & Bird LLP

(57) ABSTRACT

A terahertz imaging system uses a terahertz light source to illuminate a target object with a series of short pulses of terahertz light. The pulses have a low average output power but a high peak output power, thereby enabling imaging of the suspicious object or person at a safe distance while avoiding injury to the person being imaged. For each pulse, the reflection of the light is imaged by a detector array. The terahertz light pulses are individually narrow band and the emitted pulse train is rapidly tuned in wavelength across a wide frequency range in the terahertz band. Within the terahertz frequency range, molecules have unique absorption spectra. The energy reflected from the illuminated threat object is measured for each of the discrete narrow frequency bands and compared to the absorption spectra of known dangerous materials to determine whether the threat object contains or carries a known dangerous material.

25 Claims, 2 Drawing Sheets

TERAHERTZ IMAGING SYSTEM AND ASSOCIATED METHOD

FIELD OF THE INVENTION

Figure 1:
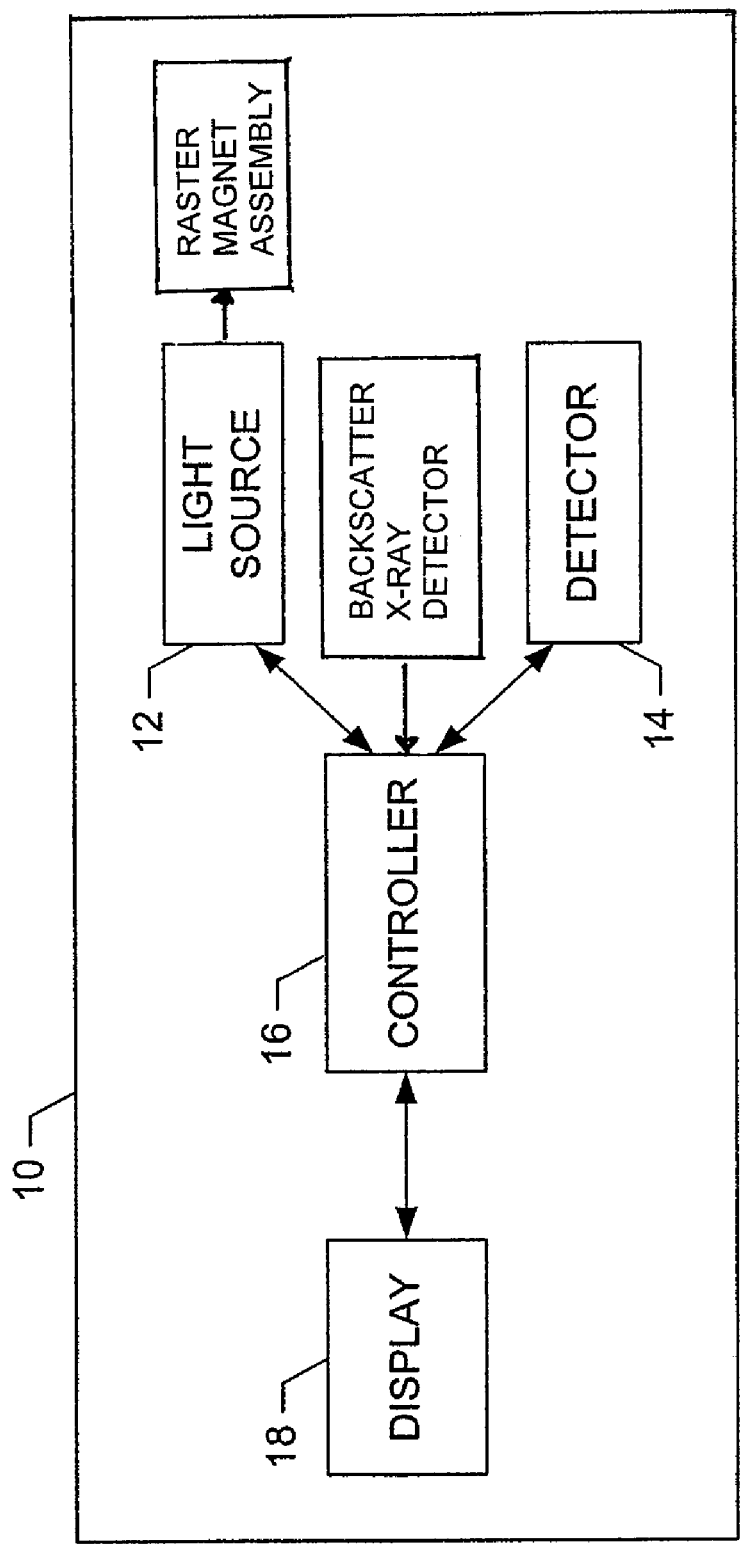

The present invention relates generally to imaging systems, and more particularly, to terahertz imaging systems.

BACKGROUND OF THE INVENTION

Chemical explosives or bombs, sometimes termed improvised explosive devices (IEDs), carried in vehicles, left behind in packages, or delivered on the person of a suicide bomber, present a threat to citizens, structures, and public transportation in the United States and to government and military installations and military personnel outside the U.S. as well. The detection of explosives in vehicles and packages, and especially on the person of suicide bombers, must be very rapid and involve minimal or no contact with the vehicles, packages, or persons. To limit the disruption of public transportation systems, passenger screening devices must minimize false positive alarms. Such screening devices must, therefore, be able to specifically identify threats.

Known systems for screening vehicles, packages, and persons include magnetometers, x-ray devices (including backscatter x-ray devices), and terahertz imaging systems. Magnetometers may be ineffective at detecting an explosive device because the device may have little or no metal content. Additionally, magnetometer screening requires coming in close proximity to the suspect package or person, such that screening personnel may be injured if an explosion occurs.

X-ray devices have been incorporated into "drive by" systems used to inspect vehicles and into personnel scanners used to detect threat objects hidden by clothing. X-ray screening devices are able to reveal hidden threat objects, however these device are only able to determine the shape and density of the hidden object. X-ray screening devices are not able to determine the specific chemical composition of the object. As such, x-ray screening devices may be ineffective at detecting an explosive device. Additionally, x-ray screening typically requires coming in close proximity to the suspect vehicle, package, or person, such that screening personnel may be injured if an explosion occurs.

Terahertz imaging systems use radio waves transmitted at terahertz frequencies (100 gigahertz (GHz) to 10 terahertz (THz)), known as terahertz radiation, to produce an x-ray-like image capable of detecting threat objects, such as those hidden under clothing. Additionally, terahertz imaging systems may be capable of determining the specific chemical composition of an imaged object by comparing the absorption spectra of a suspect object to the absorption spectra of a known threat material. However, screening using known terahertz imaging systems requires coming in close proximity to the suspect vehicle, package or person, which again may cause injury or death to screening personnel if an explosion occurs.

As such, there is a need for an imaging system capable of quickly and accurately detecting threat objects, such as explosive devices, while allowing screening personnel and equipment to maintain a safe distance from the suspect vehicle, package, or person.

BRIEF SUMMARY OF THE INVENTION

A terahertz imaging system is therefore provided that uses a terahertz light source to illuminate a target object, such as a suspicious object or person, with a series of short pulses of terahertz light. The terahertz light pulses are individually narrow band and the emitted pulse train is rapidly tuned in wavelength across a wide frequency range in the terahertz band. The pulses have a low average output power but a high peak output power, thereby enabling imaging of the suspicious object or person at a safe distance while avoiding injury to the person being imaged. For each pulse, the reflection of the light is imaged by a detector, such as a detector array. Within the terahertz frequency range, molecules have unique absorption spectra. Embodiments of the invention measure the energy reflected from the illuminated threat object for each of the discrete narrow frequency bands and compare the measurements to the absorption spectra of known dangerous materials to determine whether the threat object contains or carries a known dangerous material.

In this regard, a terahertz imaging system may comprise a terahertz light source, a detector, and a controller. The terahertz light source may be a free electron laser comprising an electron gun, a linear accelerator, and a wiggler magnet. The free electron laser may emit a plurality of output pulses across a frequency range at a target, each output pulse having a desired output frequency and a full width half maximum equal to or less than 3% of the desired output frequency. A reflection of each output pulse off the target may be received by the detector, and the received reflections may be analyzed by the controller to determine a composition material of the target based on a change in the received reflection at a predefined output frequency. The detector may be gated to the electron gun, such that the detector is activated when the electron gun is activated. The detector may use a heterodyne detection technique.

In one embodiment, the output pulses have a peak output power of 5 kilowatts to 100 kilowatts and an average output power of 1 watt to 5 watts. The frequency range may be 3 terahertz to 9 terahertz. The desired output frequency of each output pulse may be determined by at least one of an output power of an electron beam emitted by the electron gun and a separation distance between a first plurality of poles and a second plurality of poles of the wiggler magnet.

In one embodiment, the free electron laser further comprises an output coupler defining an opening through which the output pulses are emitted. A gain of each output pulse may increase as the separation distance between a first plurality of poles and a second plurality of poles decreases. As such, a size of the opening defined by the output coupler may be decreased to offset the increased gain of each output pulse.

The free electron laser may further comprise a beam redirection apparatus that receives an electron beam after a forward pass through the linear accelerator and the wiggler magnet and changes a direction of the electron beam such that the electron beam makes a reverse pass through the wiggler magnet and the linear accelerator. The reverse pass through the wiggler magnet may increase a gain of the output pulse. The reverse pass through the linear accelerator may decelerate the electron beam such that a portion of kinetic energy of the electron beam is recovered by the linear accelerator.

In one embodiment, the imaging system further comprises a raster magnet assembly and a backscatter x-ray detector. The raster magnet assembly may direct x-rays emitted by the free electron laser at the target in an x-y pattern, such that the backscatter x-ray detector may receive the x-rays reflected off the target.

The desired output frequency of the output pulses may be selected based on a predefined maximum absorption frequency of the composition material that is desirable to be detected.

In one embodiment, the imaging system further comprises at least two resonator mirrors. A position of at least one resonator mirror relative to an axis of the output pulses may be changed based on the desired output frequency.

In addition to the terahertz imaging system as described above, other aspects of the present invention are directed to corresponding methods for terahertz imaging.

BRIEF DESCRIPTION OF THE SEVERAL VIEWS OF THE DRAWING(S)

Figure 2:
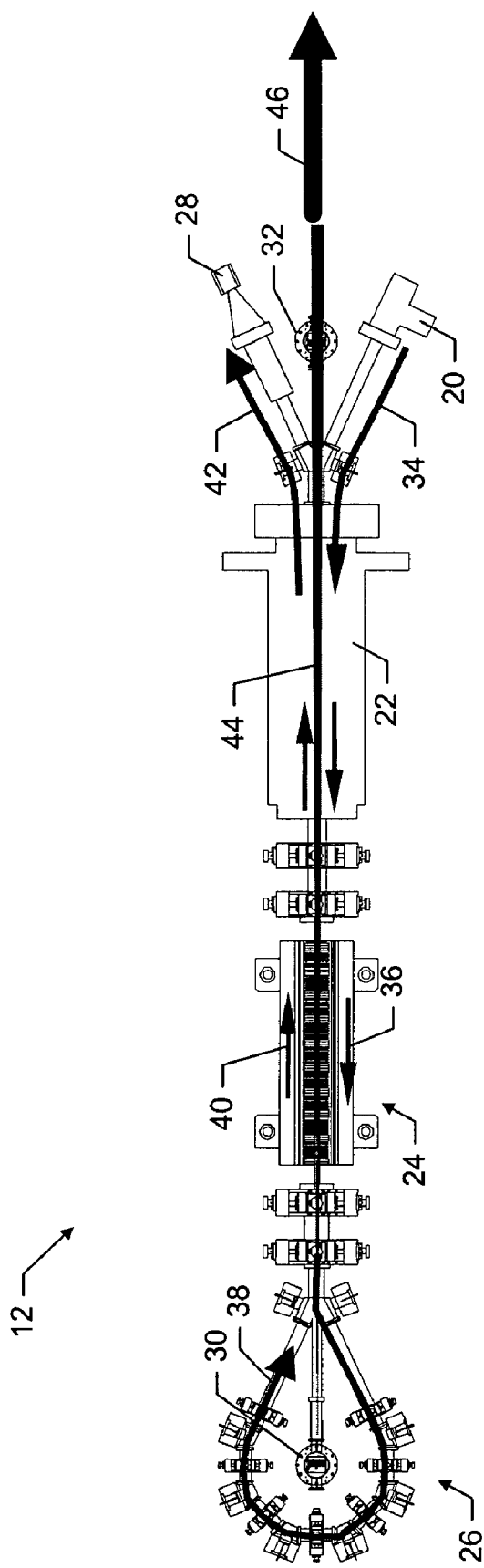

Having thus described the invention in general terms, reference will now be made to the accompanying drawings, which are not necessarily drawn to scale, and wherein:

FIG. 1 is a functional block diagram of a terahertz imaging system, according to one embodiment of the invention; and FIG. 2 is a cross-sectional view of a free electron laser of a terahertz imaging system, according to one embodiment of the invention.

DETAILED DESCRIPTION OF THE INVENTION

Embodiments of the invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring to FIG. 1, a functional block diagram of a terahertz imaging system is illustrated, according to one embodiment of the invention. The terahertz imaging system 10 comprises a terahertz light source 12, a detector 14, and a display 18. The light source and the detector may be controlled by a controller 16, which may be a computer or other microprocessor-based device. The terahertz light source 12 typically illuminates a target object with a series of short pulses of terahertz light, each pulse of light having a different frequency across a frequency range in the terahertz frequency band. For example, each pulse may differ in frequency by a predefined offset from the frequency of adjacent pulses. The frequency range may be 3 terahertz to 9 terahertz. Each output pulse has a relatively narrow bandwidth, such that the laser spectrum full width half maximum of each output pulse is equal to or less than 3%, and preferably about 1%, of the desired output frequency. Full width half maximum (FWHM) (sometimes also termed full width at half maximum) refers to the distance between points on a curve at which the signal defined by the curve is one-half of the signal's peak or maximum value. For laser spectrum FWHM, the curve defines the frequency content of the laser output pulse (i.e., the spectral distribution of the output pulse) and the peak of the curve is at the center frequency of the output pulse. In embodiments of the invention, the FWHM of 3% or less indicates that the distance between points on a curve defining the laser frequency distribution of each output pulse is equal to or less than 3% of the value of the center frequency of the output pulse. The output pulses typically have a peak output power of 5 kilowatts to 100 kilowatts and an average output power of 1 watt to 5 watts. The coherence (i.e., narrow bandwidth) of the output pulses (indicated by the FWHM of 3% or less), coupled with the relatively high peak output power, enable the terahertz imaging system to image target objects at distances sufficient to protect screening personnel. For example, embodiments of the invention may image target objects at distances greater than 10 meters.

One advantage of imaging in the terahertz frequency range is that common dry dielectric materials, such as clothing and soft-side luggage, are partially transparent to terahertz energy, thereby enabling the detection of dangerous materials behind some optically opaque barriers.

At least a portion of each output pulse that is emitted by the light source 12 is typically reflected off the target object and received by the detector 14. The detector 14 may be any suitable device capable of detecting light in the terahertz frequency range. For example, the detector may be a pyroelectric detector, such as a lithium tantalate detector. The detector may use direct imaging techniques, or alternatively may use heterodyne imaging techniques that may enable imaging at greater distances. The detector 14 may be time gated to reduce the detection of background light. As such, the detector may only be activated only when the light source is activated. The time gating may be accomplished by the controller 16, such that the controller would signal the light source to emit an output pulse and would, at approximately the same time, signal the detector to receive the reflected light.

Each received reflection may be analyzed, such as by means of the controller 16, to determine a composition material of the target based on a change in the received reflection at a predefined output frequency. Within the terahertz frequency range, molecules have unique absorption spectra. Many dangerous materials will reflect terahertz light at most wavelengths in the terahertz range, but will absorb terahertz light at one or more predefined wavelengths. Embodiments of the invention measure the energy reflected from the illuminated threat object for each of the discrete narrow frequency bands, such as by means of the detector 14, and determine at which terahertz frequency(ies) the illuminated object is absorbing the light, such as by means of the controller 16. The terahertz frequency(ies) at which the illuminated object is determined to be absorbing the light may then be compared to the known absorption spectra of dangerous materials. If the terahertz frequency(ies) at which the illuminated object is absorbing the light matches the known absorption spectra of one or more dangerous materials, then the object may contain or carry that dangerous material such that an appropriate warning may be issued. As such, terahertz imaging is capable of providing spectroscopic information regarding the imaged target object.

For example, one type of dangerous material that may be desirable to detect using a terahertz imaging system is RDX, which is an organic nitrate explosive. RDX is absorptive of light having a frequency of approximately 6.7 THz and reflective of light having other frequencies in the terahertz range. The terahertz imaging system will typically emit a series of discrete light pulses across the 3 to 9 THz frequency range at frequency intervals of 100 gigahertz (GHz), such that pulses may be emitted having a frequency of 3.0 THz, 3.1 THz, 3.2 THz, and so on through 9.0 THz. Each light pulse may have a predefined duration, such as approximately 1 to 10 microseconds, and typically 5 microseconds. Each light pulse may comprise a train of smaller micropulses, such as 10 picosecond micropulses, that all have the same frequency. The terahertz imaging system may be capable of emitting 10 to 100 output pulses per second, with a typical output of 15 pulses per second. At 15 output pulses per second, the system may scan the 6 THz frequency range, at 100 GHz intervals, in approximately 4 seconds. As each light pulse is emitted over the frequency range, the detector is gated on to receive reflections from the target object. If the target object contains or carries RDX, the detector would typically receive less reflected light from the pulses that have a frequency of or near 6.7 THz because the RDX would be absorbing more of those light pulses.

When the terahertz imaging system and, more particularly, the controller detects a known dangerous material, the system may alert the screening personnel that a particular dangerous material is present in the illuminated object. The system may also display an image of the illuminated object, and the object's surroundings within the imaging system's field of view, on a display 18. If the system displays the image that corresponds to the peak absorption wavelength of the detected material, the detected material would typically be displayed as a darker area than the rest of the image because of the increased light absorption. Alternatively, the system may highlight the location of the detected material in the image, such as by changing the color used to display the detected material.

The terahertz light source of embodiments of the invention may be a tunable-wavelength laser, such as a free electron laser. Referring now to FIG. 2, a cross-sectional view of a free electron laser is illustrated, according to one embodiment of the invention. A free electron laser 12 uses amplified radiation from a high energy electron beam. The electron beam is typically produced by an electron gun 20 and is then accelerated by a linear accelerator 22. Line 34 illustrates the path of the electron beam from the electron gun through the linear accelerator. The electron beam has a transverse energy state that is "pumped" by a periodic array of magnets (termed a wiggler magnet 24). The alternating poles of the wiggler magnet force the electrons in the beam to assume a sinusoidal path. The accelerating of the electrons along this path results in the release of a photon. Line 36 illustrates the path of the electron beam through the wiggler magnet. In the laser there is gain and an increase in laser field strength when the electron beam (the lasing medium) passes through the wiggler (the laser "pump" that excites energy states at the laser wavelength). The free electron laser typically comprises resonator mirrors 30, 32 at the ends of the beam path. The laser gain is enhanced as the light from the laser (reflected from the resonator mirrors) fills the region of the electron beam. Line 44 illustrates the laser light reflecting between the resonator mirrors within the free electron laser. This light interacts with the electric field of the electron beam and helps to stimulate additional emission and energy transfer from the electron beam into the laser light. The laser light may then be emitted through an output coupler in the resonator mirror 32. Typically, about 10% of the produced laser light will be emitted with each pass of light between the resonator mirrors. Line 46 illustrates the emission of the laser light from the free electron laser. The laser light emitted from the free electron system may be aimed at a targeted object using any suitable beam expander, such as a gold-coated parabolic mirror.

The free electron laser may also comprise an electron beam redirection apparatus 26 capable of reversing the direction of the electron beam. The beam redirection apparatus may comprise a series of permanent magnets forming a 180 degree loop in the beam pathway. Line 38 illustrates the path of the electron beam through the beam redirection apparatus. The electron beam may then pass through the wiggler magnet in the reverse direction, as illustrated by line 40. The reverse pass of the electron beam through the wiggler magnet doubles the interaction between the electron beam and the laser light and approximately doubles the laser gain.

After the reverse pass through the wiggler magnet, the electron beam will then typically pass in the reverse direction through the linear accelerator. The phase of the reverse direction electron beam will typically be timed by mechanically adjusting the transport length such that the reverse direction electron beam reenters the accelerator out of phase with the forward direction electron beam. The transport length may be adjusted using any suitable known technique, such as using a mechanical translation stage (e.g., a stepper or servo motor driven leadscrew) to move the position of the beam redirection apparatus relative to the wiggler magnet. Another technique to adjust the transport length may be to use a set of bend magnets to add an adjustable "kink" in the electron beam path. The tolerances of the transport length adjustment for a typical system may be approximately 1 to 10 thousandths of an inch. This enables the reflected beam to couple with the accelerator to add power to the electric fields in the linear accelerator, thus offsetting the power needed to drive the accelerating beam. This regenerative use of the energy from the reverse direction electron beam advantageously reduces the overall power requirement of the terahertz imaging system. Additionally, the coupling of the electron beam decelerates the reverse direction electron beam, thereby decreasing the energy and allowing the reverse direction beam to be stopped with minimal x-ray radiation. For example, the energy of the electron beam after the reverse pass through the wiggler magnet but before the reverse pass through the linear accelerator may be 3-10 megaelectronvolts (MeV). The energy of the electron beam after the reverse pass through the linear accelerator may be less than 100 kiloelectronvolts (KeV). The reverse electron beam will typically be stopped by a beam stop 28. Line 42 illustrates the path of the electron beam from the linear accelerator into the beam stop.

As discussed above, each pulse of light that is emitted by the free electron laser has a different wavelength across a frequency range in the terahertz frequency band. The wavelength of the laser light emitted by a free electron laser typically depends on the spatial period of the wiggler magnet and the wiggler magnet's transverse magnetic field intensity on the electron beam axis. The wavelength may be changed by changing at least one of three different parameters: (1) the longitudinal spacing (i.e., parallel to the electron beam path through the wiggler) of the magnetic pole pairs in the wiggler magnet; (2) the electron beam energy; and (3) the separation (i.e., perpendicular to the electron beam path through the wiggler) of the upper and lower sets of magnetic poles in the wiggler magnet (this separation may be termed the "pole gap"). Changing the wiggler magnet longitudinal spacing along the path of the beam may be mechanically challenging. Changing the electron energy may require retuning the transport magnetics used to bend the electron beam in order to recenter the electron beam. Changing the pole gap may be mechanically less difficult than the other available techniques for changing the wavelength of the output pulse, and therefore may be desirable. Changing the pole gap would typically change the strength of the magnetic field, which in turn would change the path of the electrons through the wiggler magnet (i.e., either shortening or lengthening the path), thereby changing the wavelength of the laser light. Increasing the pole gap would typically increase the wavelength and decrease the frequency of the laser light, while decreasing the pole gap would decrease the wavelength and increase the frequency of the laser light. Stepper motor driven jackscrews may be used to move the wiggler magnet poles to change the pole gap.

The laser light gain may change as the pole gap changes, with the gain typically increasing as the pole gap decreases and the gain decreasing as the pole gap increases. As discussed above, the resonator mirror 32 may comprise an output coupler defining an opening through which the output pulses are emitted. The output coupler may comprise an adjustable iris to change the size of the opening defined by the output coupler. As the frequency of the output pulse changes and the gain changes due to the corresponding pole gap change, the adjustable iris may change the size of the opening to emit more or less laser light to offset the changed gain of each output pulse, thereby keeping the power output relatively constant all wavelengths.

The round trip circulation time of the THz radiation bouncing between the resonator mirrors typically must be an integral number of THz radiation periods within a defined phase error to preserve the tuning of the free electron laser. As such, the distance between the two mirrors typically must be adjusted as the frequency of the output pulse changes. In a system having a frequency range of 3 to 9 THz, the distance between the two resonator mirrors would typically need to change by approximately 50 micrometers over the frequency range. The distance would typically be changed by moving one of the resonator mirrors, such as by using a stepper motor driven jackscrew.

Because the free electron laser of the terahertz imaging system uses a high energy electron beam, the imaging system may use the electron beam to form an x-ray beam. An X-ray is a form of electromagnetic radiation with a wavelength in the range of 10 nanometers to 100 picometers, corresponding to frequencies in the range 30 petahertz to 3 exahertz. The x-ray beam may be able to scan the target to create a penetrating radiation image that may complement the terahertz imaging spectrometry data, especially if some portion of the target cannot be accessed by terahertz radiation (e.g., solid metallic containers). The x-ray beam may be used to create a backscatter x-ray image, in which x-ray radiation that bounces back from the target is received by a backscatter x-ray detector. The output of the linear accelerator is typically allowed to drift through the wiggler magnet and be transported to a scanning or raster magnet that directs the time-gated beam pulses to small apertures arrayed in a two-dimensional pattern in an x-ray converter target. The x-ray converter target may be a hemispheric shaped electron stopping heavy metal target, and the apertures in the converter target define a pattern of x-ray beam spots that may be reflected to produce a relatively low resolution backscatter image of the target. The x-ray converter may be mechanically translated to enable the imaging system to image additional points on the target and thereby improve spatial resolution.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A terahertz imaging system comprising:
a terahertz light source for emitting a plurality of output pulses across a frequency range at a target, each output pulse having a desired output frequency and a full width half maximum equal to or less than 3% of the desired output frequency, the terahertz light source comprising an output coupler defining an opening through which the output pulses are emitted, wherein a size of the opening defined by the output coupler is configured to change to offset any change in gain of an output pulse;
a detector for receiving a reflection of each output pulse off the target; and
a controller for analyzing the reflections received by the detector for determining a composition material of the target based on a change in the received reflection at a predefined output frequency.

2. The imaging system of claim 1, wherein the terahertz light source comprises a free electron laser comprising an electron gun, a linear accelerator, and a wiggler magnet.

3. The imaging system of claim 2, wherein the terahertz light source emits output pulses having respective output frequencies that are determined by at least one of an output power of an electron beam emitted by the electron gun and a separation distance between a first plurality of poles and a second plurality of poles of the wiggler magnet.

4. The imaging system of claim 3, wherein the free electron laser further comprises the output coupler; wherein a gain of each output pulse increases as the separation distance between a first plurality of poles and a second plurality of poles decreases; wherein the size of the opening defined by the output coupler is decreased to offset the increased gain of each output pulse.

5. The imaging system of claim 2, wherein the free electron laser further comprises a beam redirection apparatus for receiving an electron beam after a forward pass through the linear accelerator and the wiggler magnet and changing a direction of the electron beam such that the electron beam makes a reverse pass through the wiggler magnet and the linear accelerator, wherein the reverse pass through the wiggler magnet increases a gain of the output pulse, and wherein the reverse pass through the linear accelerator decelerates the electron beam such that a portion of kinetic energy of the electron beam is recovered by the linear accelerator.

6. The imaging system of claim 2, wherein the free electron laser further comprises at least two resonator mirrors, wherein a position of at least one resonator mirror relative to an axis of the output pulses is changed based on the desired output frequency.

7. The imaging system of claim 1, wherein the terahertz light source emits output pulses having a peak output power of 5 kilowatts to 100 kilowatts and an average output power of 1 watt to 5 watts.

8. The imaging system of claim 1, wherein the terahertz light source emits output pulses over a frequency range of 3 terahertz to 9 terahertz.

9. The imaging system of claim 1, wherein the terahertz light source emits output pulses having respective output frequencies that are selected based on a predefined maximum absorption frequency of the composition material that is desirable to be detected.

10. The imaging system of claim 1, wherein the detector uses a heterodyne detection technique.

11. A terahertz imaging system comprising:
a terahertz light source for emitting a plurality of output pulses across a frequency range at a target, each output pulse having a desired output frequency and a full width half maximum equal to or less than 3% of the desired output frequency;
a detector for receiving a reflection of each output pulse off the target;
a controller for analyzing the reflections received by the detector for determining a composition material of the target based on a change in the received reflection at a predefined output frequency;
a raster magnet assembly for directing x-rays emitted by the terahertz light source at the target; and
a backscatter x-ray detector for receiving the x-rays reflected off the target.

12. A terahertz imaging system comprising:
a free electron laser comprising an electron gun, a linear accelerator, and a wiggler magnet, wherein the free electron laser emits a plurality of output pulses across a frequency range at a target, each output pulse having a desired output frequency, wherein the free electron laser further comprises an output coupler defining an opening through which the output pulses are emitted, wherein a size of the opening defined by the output coupler is configured to change to offset any change in gain of an output pulse;
a beam redirection apparatus for receiving an electron beam after a forward pass through the linear accelerator and the wiggler magnet and changing a direction of the electron beam such that the electron beam makes a reverse pass through the wiggler magnet and the linear accelerator, wherein the reverse pass through the wiggler magnet increases a gain of each output pulse, and wherein the reverse pass through the linear accelerator decelerates the electron beam such that a portion of kinetic energy of the electron beam is recovered by the linear accelerator;
a detector for receiving a reflection of each output pulse off the target; and
a controller for analyzing the reflections received by the detector for determining a composition material of the target based on a change in the received reflection at a predefined output frequency.

13. The imaging system of claim 12, wherein the free electron laser emits output pulses having a peak output power of 5 kilowatts to 100 kilowatts and an average output power of 1 watt to 5 watts.

14. The imaging system of claim 12, wherein the free electron laser emits output pulses over a frequency range of 3 terahertz to 9 terahertz.

15. The imaging system of claim 12, wherein the free electron laser emits output pulses having respective output frequencies determined by at least one of an output power of an electron beam emitted by the electron gun and a separation distance between a first plurality of poles and a second plurality of poles of the wiggler magnet.

16. The imaging system of claim 15, wherein a gain of each output pulse increases as the separation distance between a first plurality of poles and a second plurality of poles decreases; and wherein the size of the opening defined by the output coupler is decreased to offset the increased gain of each output pulse.

17. The imaging system of claim 12, wherein the detector is gated to the electron gun, such that the detector is activated when the electron gun is activated.

18. The imaging system of claim 12, wherein the free electron laser emits output pulses having respective output frequencies that are selected based on a predefined maximum absorption frequency of the composition material that is desirable to be detected.

19. The imaging system of claim 12, wherein the free electron laser further comprises at least two resonator mirrors, wherein a position of at least one resonator mirror relative to an axis of the output pulses is changed based on the desired output frequency.

20. The imaging system of claim 12, wherein the detector uses a heterodyne detection technique.

21. A terahertz imaging system comprising:
a free electron laser comprising an electron gun, a linear accelerator, and a wiggler magnet, wherein the free electron laser emits a plurality of output pulses across a frequency range at a target, each output pulse having a desired output frequency;
a beam redirection apparatus for receiving an electron beam after a forward pass through the linear accelerator and the wiggler magnet and changing a direction of the electron beam such that the electron beam makes a reverse pass through the wiggler magnet and the linear accelerator, wherein the reverse pass through the wiggler magnet increases a gain of each output pulse, and wherein the reverse pass through the linear accelerator decelerates the electron beam such that a portion of kinetic energy of the electron beam is recovered by the linear accelerator;
a detector for receiving a reflection of each output pulse off the target;
a controller for analyzing the reflections received by the detector for determining a composition material of the target based on a change in the received reflection at a predefined output frequency;
a raster magnet assembly for directing x-rays emitted by the free electron laser at the target in an x-y pattern; and
a backscatter x-ray detector for receiving the x-rays reflected off the target.

22. The imaging system of claim 21, wherein the free electron laser emits output pulses having a full width half maximum equal to or less than 3% of the desired output frequency.

23. A method of terahertz imaging, the method comprising:
emitting a plurality of output pulses across a frequency range at a target, each output pulse having a desired output frequency and a full width half maximum equal to or less than 3% of the desired output frequency, wherein emitting the plurality of output pulses comprises changing a size of an opening of an output coupler through which the output pulses are emitted to offset any change in gain of an output pulse;
receiving a reflection of each output pulse off the target; and
analyzing the received reflections to determine a composition material of the target based on a change in the received reflection at a predefined output frequency.

24. The method of claim 23, wherein emitting the plurality of output pulses comprises emitting output pulses having a peak output power of 5 kilowatts to 100 kilowatts and an average output power of 1 watt to 5 watts.

25. The method of claim 23, wherein emitting the plurality of output pulses comprises emitting output pulses over a frequency range of 3 terahertz to 9 terahertz.

* * * * *